(12) United States Patent
Kreisler et al.

(10) Patent No.: US 8,831,181 B2
(45) Date of Patent: Sep. 9, 2014

(54) GRID MODULE OF A SCATTERED-RADIATION GRID, MODULAR SCATTERED-RADIATION GRID, CT DETECTOR AND CT SYSTEM

(75) Inventors: Björn Kreisler, Erlangen (DE); Thomas Reichel, Heroldsbach (DE); Bodo Reitz, Forchheim (DE); Helmut Winkelmann, Eggolsheim (DE); Stefan Wirth, Erlangen (DE); Jan Wrege, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 157 days.

(21) Appl. No.: 13/480,717

(22) Filed: May 25, 2012

(65) Prior Publication Data

US 2012/0300898 A1 Nov. 29, 2012

(30) Foreign Application Priority Data

May 26, 2011 (DE) .......................... 10 2011 103 851

(51) Int. Cl.
*G21K 1/00* (2006.01)
*G21K 1/02* (2006.01)
(52) U.S. Cl.
CPC ..................................... *G21K 1/025* (2013.01)
USPC ........................................................ 378/154
(58) Field of Classification Search
CPC .... A61B 6/032; A61B 6/4291; A61B 6/4014; G21K 1/025
USPC ........................ 378/145, 153, 154; 250/505.1
See application file for complete search history.

(56) References Cited

U.S. PATENT DOCUMENTS

| | | |
|---|---|---|
| 5,949,850 A | 9/1999 | Tang |
| 6,363,136 B1 | 3/2002 | Flisikowski et al. |
| 6,707,884 B1 | 3/2004 | Ogawa |
| 2007/0025518 A1 | 2/2007 | Elgali et al. |
| 2007/0064878 A1 | 3/2007 | Heismann |
| 2007/0152159 A1 | 7/2007 | Hoffman et al. |
| 2007/0258566 A1 | 11/2007 | Eckenbach |
| 2011/0019801 A1 | 1/2011 | Eichenseer et al. |

FOREIGN PATENT DOCUMENTS

| | | |
|---|---|---|
| CN | 1965373 A | 5/2007 |
| CN | 101964217 A | 2/2011 |
| DE | 19947537 A1 | 4/2001 |
| DE | 102008030893 A1 | 12/2009 |
| DE | 102010011581 A1 | 2/2011 |
| JP | 2009050654 A | 3/2009 |

OTHER PUBLICATIONS

German Priority Document DE 10 2011 103 851.9 filed May 28, 2011 (not yet published).
German Office Action May 9, 2012 for German Patent Application No. 10 2011 103 851.9.
Chinese Office Action and English translation thereof dated Feb. 24, 2014.

*Primary Examiner* — Courtney Thomas
(74) *Attorney, Agent, or Firm* — Harness, Dickey & Pierce, P.L.C.

(57) ABSTRACT

A grid module of a scattered-radiation grid is disclosed. The scattered-radiation grid includes a number of grid modules disposed next to one another with a plurality of webs, especially for use in conjunction with a CT detector, a CT detector and a CT system with such a detector. In accordance with an embodiment of the invention, at the joining surfaces of the grid modules, the webs located there are provided with breakthroughs to compensate for a disproportionate reduction in scattered radiation.

29 Claims, 7 Drawing Sheets

GRID MODULE OF A SCATTERED-RADIATION GRID, MODULAR SCATTERED-RADIATION GRID, CT DETECTOR AND CT SYSTEM

PRIORITY STATEMENT

The present application hereby claims priority under 35 U.S.C. §119 to German patent application number DE 10 2011 103 851.9 filed May 26, 2011, the entire contents of which are hereby incorporated herein by reference.

FIELD

At least one embodiment of the invention generally relates to a grid module of a scattered-radiation grid, to a scattered-radiation grid including a number of grid modules with grid webs arranged next to one another, especially for use in conjunction with a CT detector, to a CT detector and to a CT system with such a detector.

BACKGROUND

Scattered-radiation grids—more precisely scattered-radiation collimators embodied in a grid shape—for CT detectors are generally known and are used in almost every CT system currently employed in practice. Such scattered-radiation grids are of importance in particular in dual-source CT systems with two emitter/detector systems offset at an angle to each other on the gantry, since the amount of scattered radiation from an emitter system operated in parallel and offset at an angle is especially high.

In relation to a scattered-radiation grid of modular construction the reader is referred to German publication DE 10 2008 030 893 A1 for example.

One problem with such modular scattered-radiation grids with a number of grid modules arranged next to one another however lies in the fact that artifacts occur in the area of the joint between two grid modules in the projections recorded therewith, which have a negative effect on the image quality of a tomographic image dataset reconstructed from such projections or generate visible artifacts in the tomographic image respectively.

SUMMARY

An embodiment of the invention is directed to a modular scattered-radiation grid in which projection artifacts are largely suppressed.

Advantageous developments of the invention are the subject matter of subordinate claims.

In accordance with this basic idea, the inventors in at least one embodiment propose improving a grid module for a scattered-radiation grid consisting of a number of grid modules arranged next to one another, each equipped with a plurality of grid webs, such that on at least one edge side of the grid module, a grid web running there along the at least one edge side is embodied at least partly perforated at a plurality of sections.

A detector of a CT system with a modular-construction inventive scattered-radiation grid and also a CT system with such a detector is additionally proposed as part of an embodiment of the invention.

BRIEF DESCRIPTION OF THE DRAWINGS

The invention is described in greater detail below with reference to the example embodiments with the aid of the figures, with only the features necessary for understanding the invention being presented. The reference characters used are as follows: 1: CT system; 2: First x-ray tube; 3: First detector; 4: Second x-ray tube; 5: Second detector; 6: Gantry housing; 7: Patient; 8: Examination table; 9: System axis; 10: Control and processing system; B: Upper and lower continuous edge-side web; D: Detector element; d: Thickness of the webs; F: Plastic film; G: Scattered radiation grid; GM: Grid module; h: Height of the webs; l: Length of the webs; L: Joint line (joint surface); O: Breakthrough; Prg1-Prgn: Computer programs; S: Web.

The individual figures are as follows.

DETAILED DESCRIPTION OF THE EXAMPLE EMBODIMENTS

Figure 1:
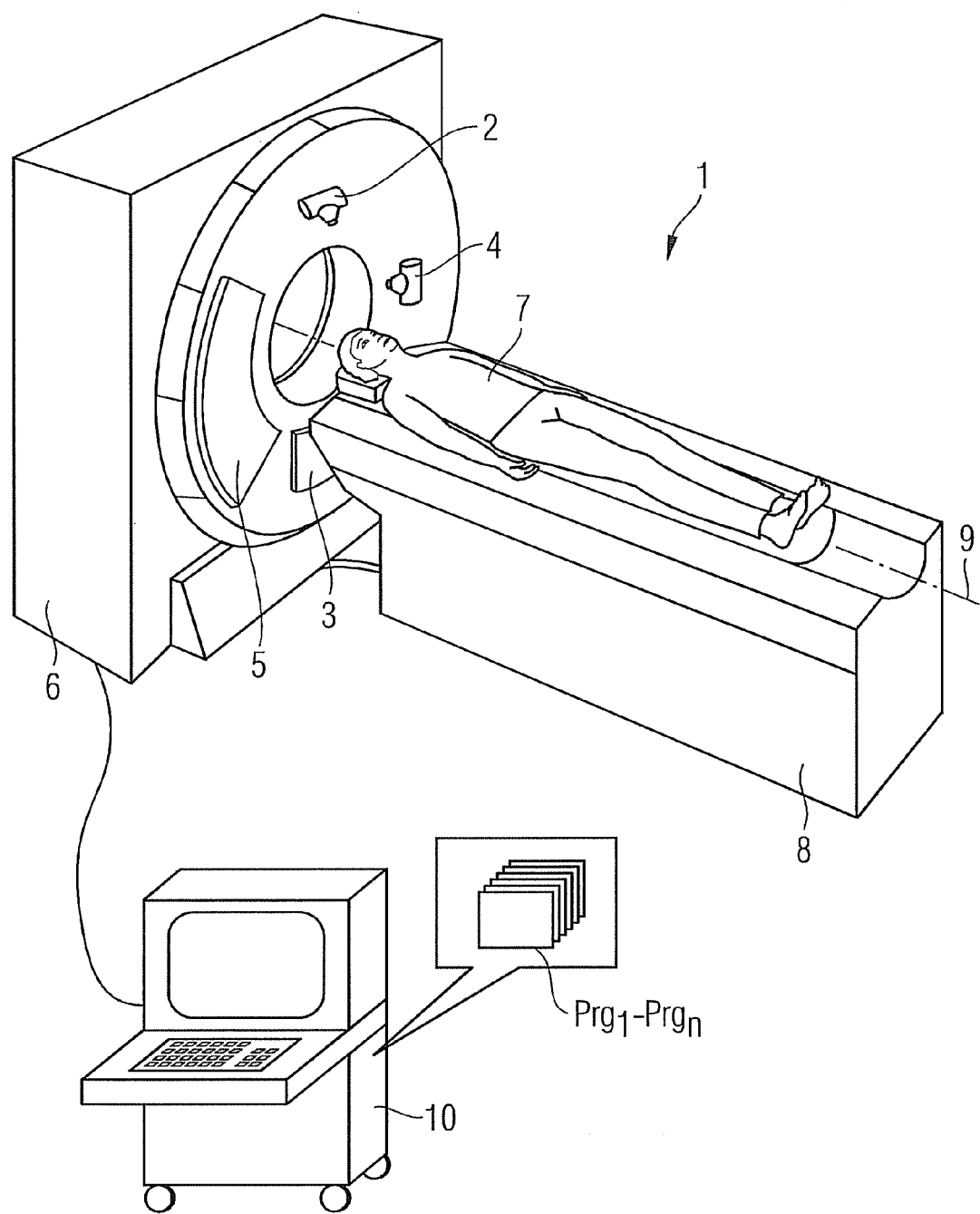
FIG. 1: CT system with CT detectors with an embodiment of the inventive scattered-radiation grids.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between;" "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/ or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventors have recognized that the artifacts in the, area of the joints of grid modules of a modular-design scattered-radiation grid essentially arise as a result of a wall thickening of the grid webs occurring in these joint areas because of the doubled walls in these areas and, through this, scattered radiation arriving from the side—in relation to the other, non-doubled grid webs—being more heavily suppressed. Basically, although a greater suppression of scattered radiation would be advantageous, an increased scattered radiation suppression only locally at specific points generates undesired artifacts.

In order to avoid this excessive suppression, it would basically be possible to halve the wall thicknesses of the webs of the grids at the joints of the grid modules, so that ultimately, at the joint between two webs, the same, i.e. single, web thickness occurs as at all other webs of the scattered-radiation grid. However such a measure would greatly increase the production costs.

To solve this problem, the inventors in at least one embodiment thus propose to provide the grid webs abutting each other and thus forming thicker grid webs with a plurality of breakthoughs, so that overall the material occupancy of the adjoining grid webs available for shielding against scattered radiation is reduced and thereby the increased shielding of the scattered radiation through the construction-related strengthening of the overall web thickness is simply compensated for by the material reduction in the grid webs. Since with this the sum of the non-shielded scattered radiation again corresponds to the value without thickening of the grid web, the artifacts which arise through a disproportionately high scattered radiation shielding at the joints of two grid modules are avoided by this measure.

Use is also made of the fact that a reduced material occupancy of the web of a scattered-radiation grid increasingly lets scattered radiation pass through to the detector module lying underneath. The reduction of the material occupancy can occur within the meaning of the invention by cutouts or breakthroughs being created in the lateral grid webs of the grid module. Through this measure the disproportionate shielding of scattered radiation by doubled webs at the joints can be compensated for such that the detector elements at the joints of the grid modules are also shielded with the same effectiveness as detector elements disposed centrally in relation to the grid module.

Since the basic assumption is to be made that the shielding effect of a thickened grid web not only relates to the detector element in the immediate vicinity or in the adjacent row or column of detector elements, but also to detector pixels of the next and next-but-one row or column lying towards the middle of the grid module, the attenuation affect extending to these rows or columns can thus be compensated for in an improved embodiment likewise by an, albeit smaller, reduction of the material occupancy of the next grid web and if necessary the grid web lying further inwards in the grid module. For this breakthroughs must merely—inwards with decreasing overall surface, be inserted into the grid webs, which reduce the occupancy density of the grid webs.

In accordance with this basic idea, the inventors in at least one embodiment propose improving a grid module for a scattered-radiation grid consisting of a number of grid modules arranged next to one another, each equipped with a plurality of grid webs, such that on at least one edge side of the grid module, a grid web running there along the at least one edge side is embodied at least partly perforated at a plurality of sections.

Advantageously the at least partly perforated sections and non-perforated sections can alternate in such cases.

In addition the grid module can be embodied so that it has at least two grid webs with breakthroughs opposite one another and on an edge side. Such grid modules can be predominantly arranged in a single row to form a scattered radiation grid alongside one another such that only the grid webs of two modules provided with breakthroughs lie next to one another.

It is also useful for the breakthroughs, seen in the longitudinal direction of the webs, to be disposed at the same distances from one another.

In an embodiment in such cases exclusively one breakthrough can be arranged at least one longitudinal position of the at least one grid web in each case. In other words a plurality of breakthroughs is distributed over the length of the grid web, with exclusively one single breakthrough being disposed at each longitudinal position of the breakthroughs. The side surface of the edge side grid web thus takes on a strip pattern with a plurality of strips consisting of breakthroughs which run from top to bottom, i.e. at right angles to the longitudinal direction of the grid web.

As an alternative to this, a number of breakthroughs can be arranged in each case at least one longitudinal position of the at least one grid web along the web height. For example a checkerboard-like pattern of breakthroughs and intact material or also a strip pattern of a number of strips running in the longitudinal direction of the grid web can arise.

It is also advantageous for the breakthroughs on at least two opposing grid webs to the disposed in such a way and embodied in relation to their size such that all breakthroughs of a grid web lie opposite a breakthrough-free surface of the other edge-side grid web in each case. The breakthroughs of two grid webs of the same module lying opposite each other on the edge side are arranged offset. This is especially advantageous because, with grid modules arranged in this way next to one another, the grid webs adjoining one another of two modules the breakthroughs are arranged offset to one another so that, relative to a lateral projection the material occupancy essentially corresponds to a single web and thus the scattered radiation absorbing effect of only a single grid web is generated.

Furthermore, in relation to the height of the at least one edge-side grid web, the number of breakthroughs can be embodied equal to the number of breakthrough-free surfaces.

For subsequent assembly of a number of grid modules into a complete scattered-radiation grid it is also especially useful, at the minimum and/or maximum height of the at least one edge-side grid web, for a continuous area without breakthroughs to be embodied over the entire length of the grid web. This uninterrupted area prevents the grid modules catching on each other, which could possibly lead to damage to the exposed webs.

In order to compensate for the effect of undesirably increased scattered radiation shielding in the edge area of the grid modules, it can also be useful, for grid webs adjacent to the grid webs disposed on the edge side, i.e. grid webs further inwards in the grid module, to have lateral breakthroughs.

Since the effect of the excessive scattered radiation shielding in the edge area reduces from the edge inwards, the number and/or overall surface of the breakthroughs in the grid webs should also likewise reduce accordingly from the grid webs of the edge area of the grid module to the center of the grid module.

The proposed grid modules can have grid webs both exclusively parallel in one direction and also crossing each other, preferably crossing each other at right angles.

To avoid possible mechanical damage to the grid module at least one inventively embodied edge-side grid web can additionally be provided from the outside with a plastic film. This produces a less sensitive unbroken outer side which during assembly has less of the tendency to catch on other grid modules.

In addition to the grid modules embodied in accordance with an embodiment of the invention a scattered-radiation grid for an x-ray detector of a CT system is proposed with a plurality of detector elements disposed in rows and columns over its surface, comprising:

At least two grid modules disposed next to one another,
With each grid module possessing a number of grid webs arranged next to one another with irradiation zones lying between them, and
At least one edge-side web of a grid module being adjacent and running in parallel to the at least one other edge-side web of another grid module with no irradiation zone disposed between them.

An improvement of at least one embodiment in this case lies in the fact that the grid webs running adjacent to one another and without an irradiation zone lying between them each have a plurality of lateral breakthroughs.

In this case the lateral breakthroughs of adjacent edge-side grid webs can be arranged such that the breakthroughs of one grid web are covered in each case by the other grid web adjacent to the edge side.

Furthermore the breakthroughs can be dimensioned as regards their number and distribution such that through the breakthroughs the increased scattered radiation reduction as a result of the double grid webs present is compensated for in the edge area of the grid modules.

Apart from that the previously described grid modules can advantageously be used.

A detector of a CT system with a modular-construction inventive scattered-radiation grid and also a CT system with such a detector is additionally proposed as part of an embodiment of the invention.

FIG. 1 shows a schematic diagram of an inventive CT system 1. The CT system 1 has a first emitter/detector system with an x-ray tube 2 and a detector 3 lying opposite it and a second emitter/detector system disposed offset at an angle on the gantry not shown explicitly here, with a second x-ray tube 4 with a detector 5 opposite it. The gantry is located in a gantry housing 6 and rotates the emitter/detector systems during the scanning around a system axis 9. The patient 7 to be examined is located on a movable examination table 8, which is either pushed continuously or sequentially along the system axis 9 through the scanning field located in the gantry housing 6, with the attenuation of the x-ray radiation emitted by the x-ray tubes being measured by the detectors. The operation of the CT system 1 is controlled with the aid of a control and processing system 10, which features computer programs Prg1 through Prgn which execute the control routines necessary for operation, carry out data editing and also perform the reconstruction of image datasets.

The two emitter/detector systems of an embodiment feature inventive modular-construction scattered-radiation grids which screen out the scattered radiation occurring during operation and, as exclusively as possible are intended to let the radiation emitted directly from the x-ray tubes of the respective emitter/detector system, after its attenuation by the patient, strike the detector elements of the detector. Because of the simultaneous operation of the two x-ray tubes 2 and 4 it is particularly necessary to screen out scattered radiation occurring during the operation of the tubes 2 and 4. Scattered radiation grids can especially be used for this purpose, which have webs crossing one another, as are shown in the subsequent figures.

It is however also pointed out that scattered-radiation grids with webs running exclusively in parallel fall within the scope of the invention.

Figure 2:
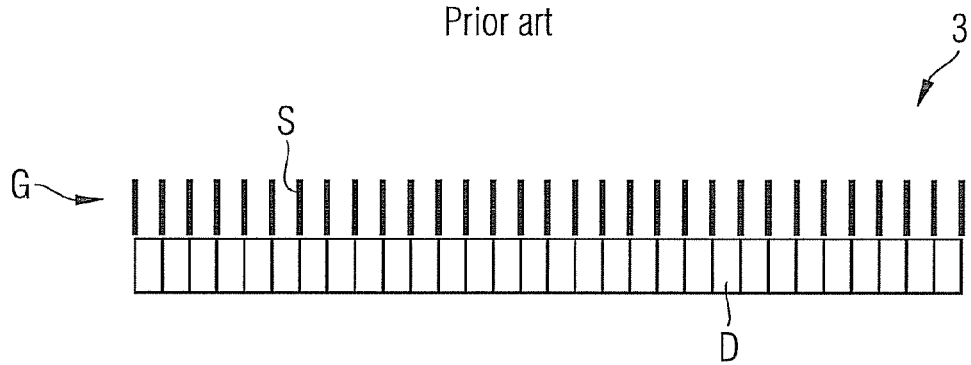
FIG. 2: Longitudinal section through a CT detector with scattered radiation grid lying above it.

An example of a detector 3 constructed from a plurality of detector elements D disposed next to one another like a checkerboard, with a scattered-radiation grid G lying above them comprising a plurality of webs S, is shown in longitudinal section in FIG. 2.

Figure 3:
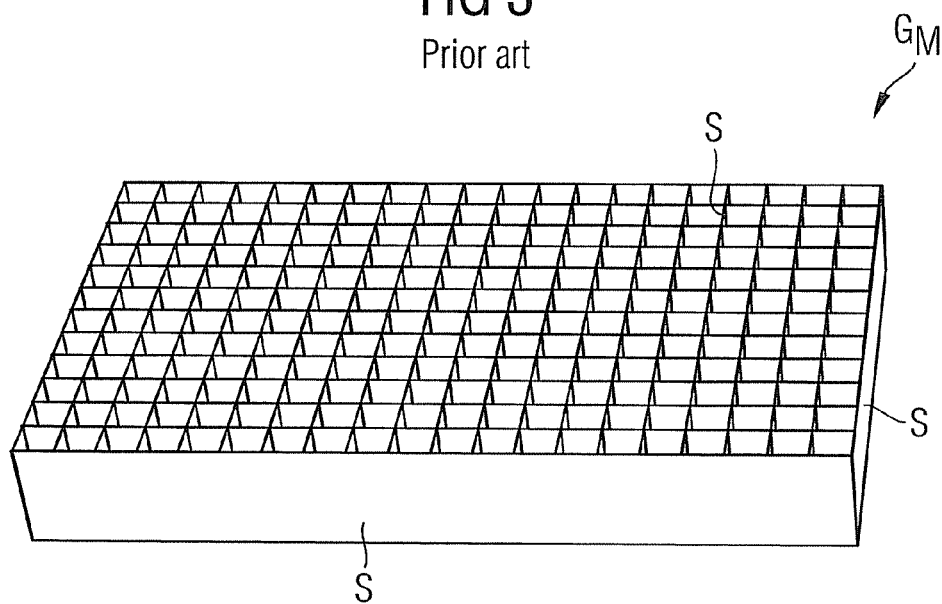
FIG. 3: 3D view of a grid module obliquely from above.
Figure 4:
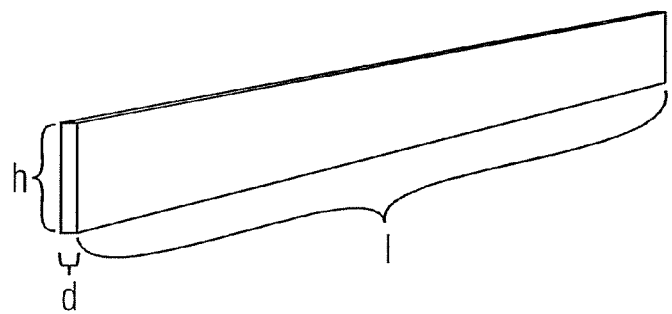
FIG. 4: Lateral 3D view of an individual grid module.

FIG. 3 shows a known grid module GM with a number of grid webs S crossing each other at right angles in a 3D view obliquely from above. To avoid possible confusion of terms, in FIG. 4, which shows an individual grid web S in a 3D view, the length l, the height h and the depth d are entered in the diagram.

Figure 5:
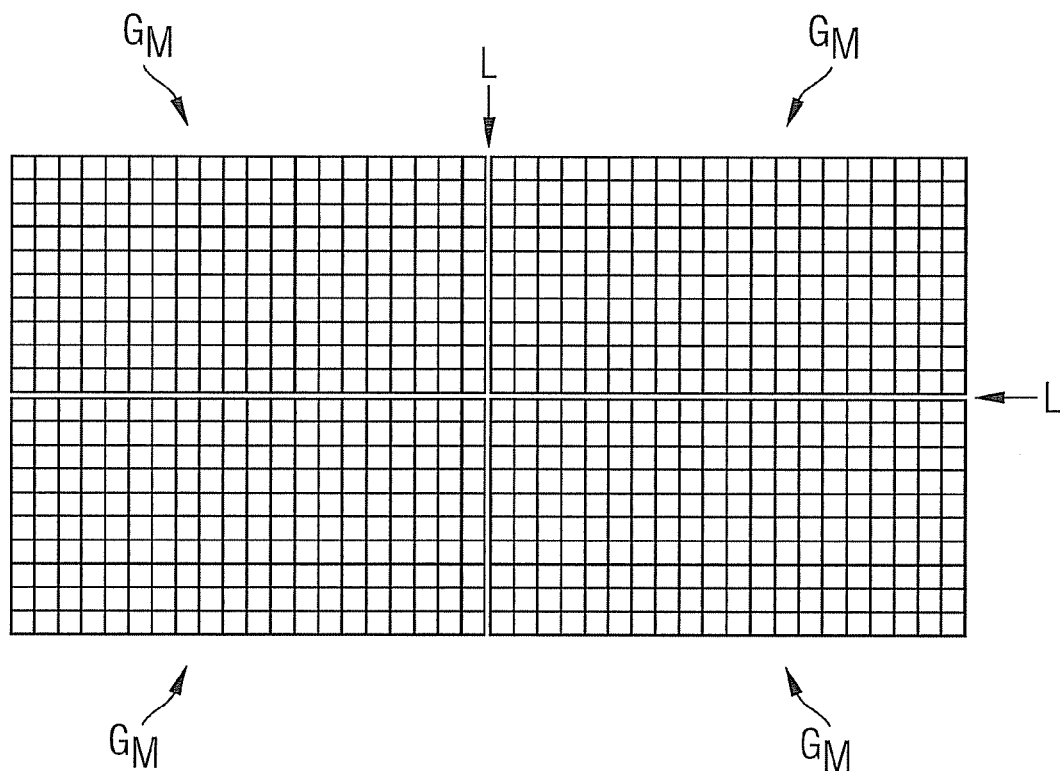
FIG. 5: Overhead view of four grid modules disposed next to one another.
Figure 6:
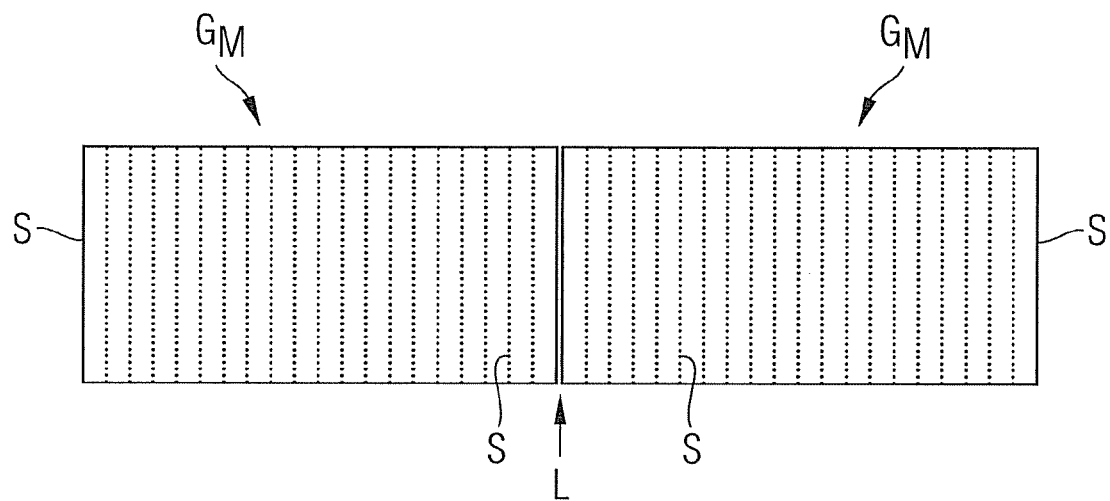
FIG. 6: Side view of the grid modules from FIG. 5.

FIG. 5 shows four grid modules GM disposed next to one another in an overhead view, with the webs S of grid modules GM doubling at the joint line L and thus adding to each other in relation to their overall effective depth. These grid modules GM are shown again in FIG. 6 in a view from the side. Here too it can be recognized that the overall depth of the web material—which at all points has the same wall width, i.e. depth—doubles at the joint line L, by which scattered incident radiation is increasingly absorbed. Thus the detector elements adjacent to such doubled grid webs are heavily shielded from scattered radiation and this produces artifacts in the recorded projections and thus also image artifacts in reconstructed tomographic representations.

To avoid this excessive scattered-radiation reduction and the image artifacts associated therewith, by explicit introduction of gaps or breakthroughs in the outer walls, the wall thickness and thus the absorption capability of an immediately adjacent pair of grid webs can be reduced and preferably bought to the same level as that of the other centrally-arranged grid webs.

Figure 7:
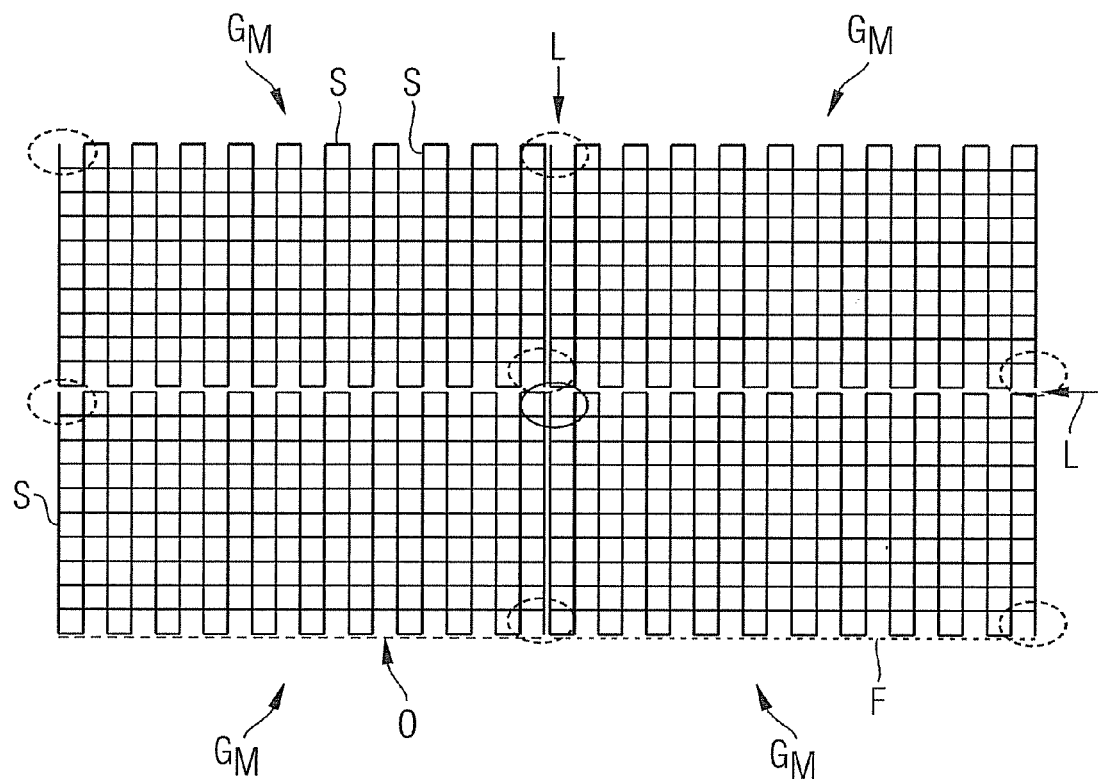
FIG. 7: Overhead view of four inventive grid modules disposed next to one another.

In the first of the variants shown in FIG. 7-*four* identical grid modules GM are shown—breakthroughs O are only created or parts of walls are removed here in the φ direction of the detector module. In the z-direction the grid webs S remain at their full thickness. Overall this produces a serpentine outer wall on the grid module. At two corners in each case a freestanding end of grid web is produced. This could however also be omitted since the respective next module possesses a wall there. As a supplement an optional plastic foil F is shown on one side of the serpentine outer wall of the grid module GM, which allows a simpler assembly of the scattered-radiation grid.

Figure 8:
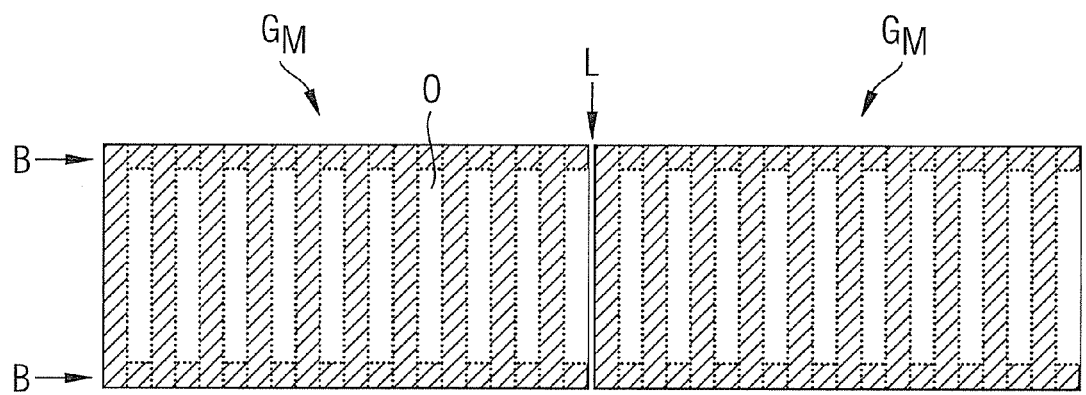
FIG. 8: Side view of the grid modules from FIG. 7.

FIG. 8 shows a side view of the grid module GM from FIG. 7, with, at a number of longitudinal positions of the grid web to be seen on the outside, the breakthroughs O passing from the top to the bottom can be seen in the outer grid web. Overall the serpentine outer wall of the grid module GM is produced in this way. In the upper and lower area of the grid web end-to-end bars B can be seen, which during assembly of a number of grid modules GM, ensure that these do not hook into each other and thereby damage each other.

Figure 9:
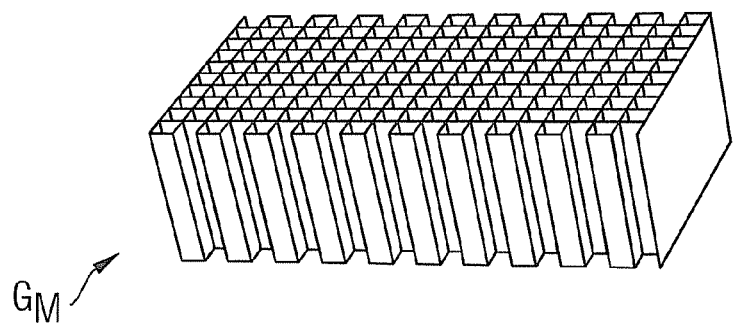
FIG. 9: 3D view of a grid module from FIG. 7.

FIG. 9 shows a supplementary 3D view of such a grid module GM, with—for technical reasons—the upper and lower end-to-end bars B not been shown however.

Figure 10:
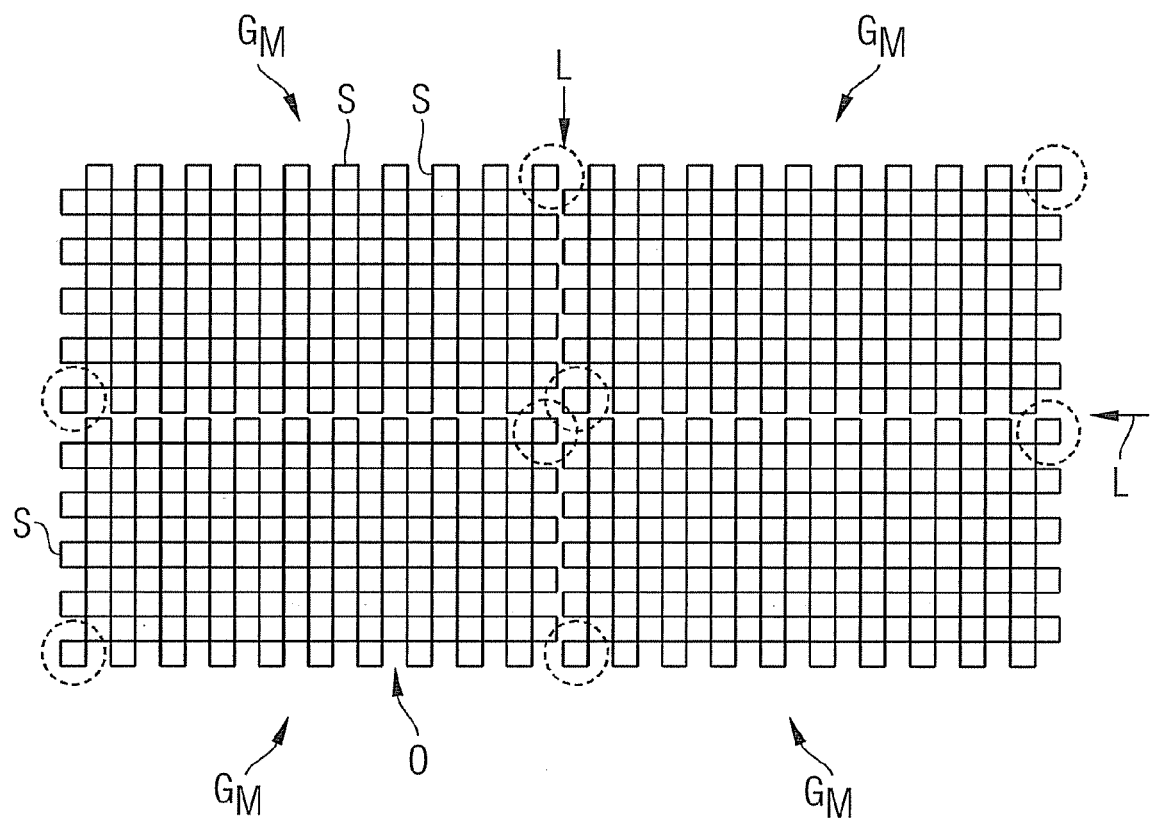
FIG. 10: Overhead view of four grid modules disposed next to one another.

A second variant of an embodiment of an inventive grid module GM is shown in FIG. 10. The structure is similar to the grid modules shown in FIG. 7-9, however the adaptation is carried out here both for the ϕ-outer wall and for the z-outer wall, i.e. respective outer grid web pairs lying opposite one another. Thus the entire lateral outer side of such a grid module GM has a serpentine-shaped surface structure. At the points highlighted by the dashed-line circles, however, structures are also produced in such cases (thick foot) that are mechanically sensitive, but are less susceptible however than the individual free walls occurring in the first variant (see dashed-line ellipses in FIG. 7).

Figure 11:
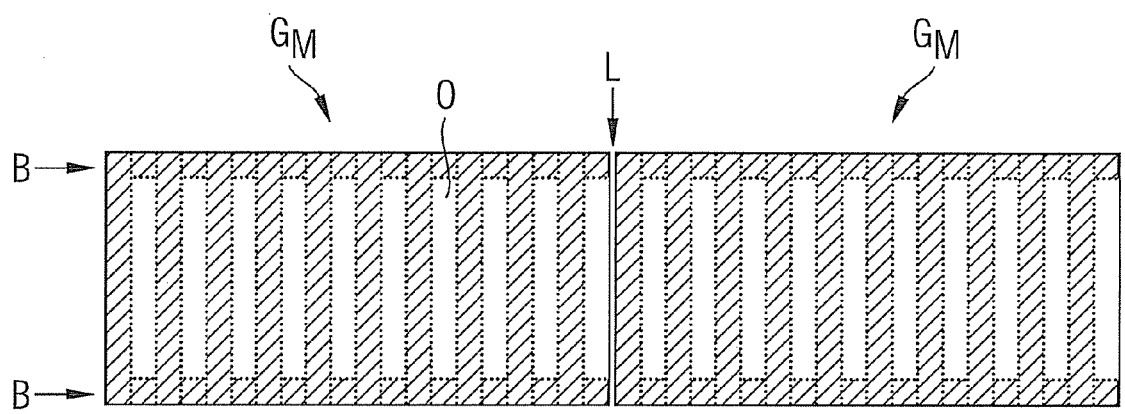
FIG. 11: Side view of the grid modules from FIG. 10.

FIG. 11 once again shows a side view of the grid module GM from FIG. 10, with end-to-end bars "B" also being recognizable here in the upper part and lower area of the grid web to be seen, which on assembly of a number of grid modules GM, ensure that these do not hook into each other and thus damage each other.

Figure 12:
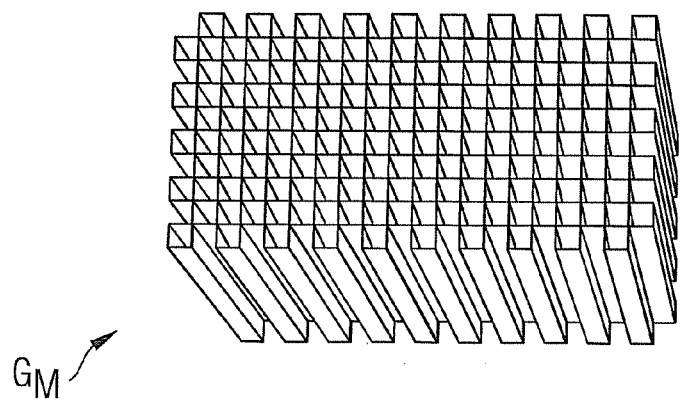
FIG. 12: 3D view of a grid module from FIG. 10.

FIG. 12 once again shows a supplementary 3D view of such a grid module GM, with—for technical reasons—the upper and lower end-to-end bars B not being shown.

Figure 13:
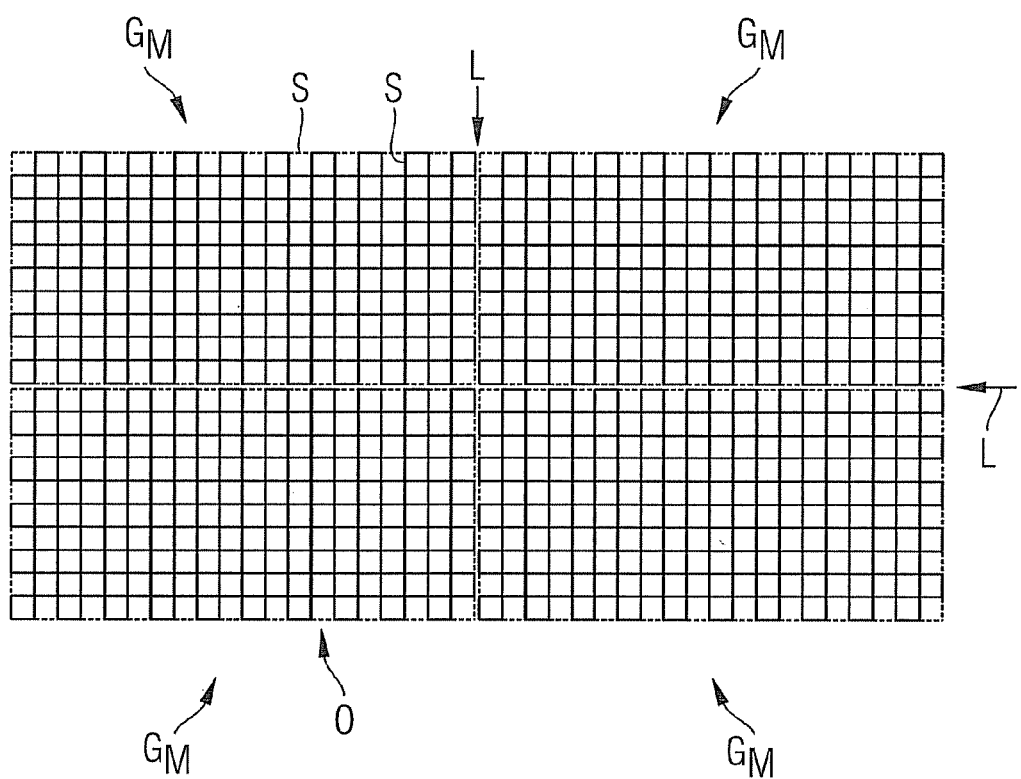
FIG. 13: Overhead view of four grid modules disposed next to one another.
Figure 14:
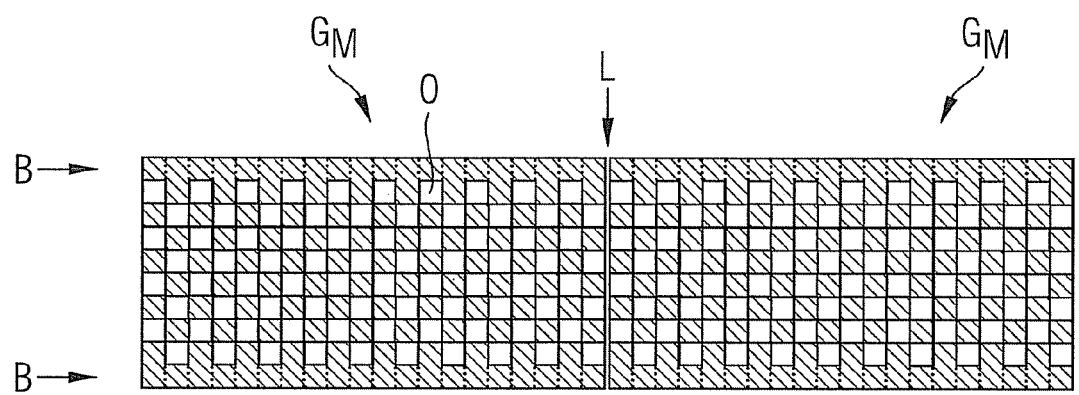
FIG. 14: Side view of the grid modules from FIG. 13.

A third variant of an embodiment of the inventive grid module GM is shown in FIGS. 13 and 14, with cutouts being made here in the outer grid webs S like a checkerboard, which are arranged offset on the respective opposing edge-side grid web. Overall the effect of these—except for the upper and lower bars present if necessary—on assembly of these grid modules GM into a complete scattered-radiation grid, is not to cause any increased shielding of the scattered radiation even at the joint lines L (seen in three dimensions: joint surface)—in relation to the remaining grid webs. In addition mechanically oversensitive parts are avoided with such an embodiment.

Such a grid module can be manufactured with known technology since the currently possible minimum wall thickness of around 80 μm does not need to be exceeded. The necessary precision of manufacturing and the positioning is not influenced. Such a grid module no longer possesses smooth outer walls. Therefore it is likely to have to be handled with a little more care than previous grid modules with smooth outer walls. If such interrupted outer walls prove to be a problem to handle, a thin, slightly absorbent plastic film could be glued on as an addition.

Overall an embodiment of the invention proposes a grid module of a scattered-radiation grid, a scattered-radiation grid comprising a number of grid modules arranged next to one another with a plurality of webs, especially for use in conjunction with a CT detector, a CT detector with a modular scattered-radiation grid and a CT system with such a detector, with inventively, at the joint surfaces of the grid modules the webs located there being provided with breakthroughs to compensate for disproportionate reduction in scattered radiation.

Although the invention has been illustrated and described in greater detail by the preferred exemplary embodiment, the invention is not restricted by the disclosed examples and other variants can be derived herefrom by the person skilled in the art, without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A grid module of a scattered-radiation grid comprising a number of grid modules disposed next to one another, each of the grid modules being equipped with a plurality of grid webs, wherein, on at least one edge side of at least one of the grid modules, a grid web running along the at least one edge side is designed to be broken through at least partly at a plurality of sections.

2. The grid module of claim 1, wherein the at least partly broken-through sections and non-broken-through sections are arranged alternately.

3. The grid module of claim 1, wherein on at least one edge side of at least one of the grid modules, at least two grid webs are present with the at least partly broken-through sections opposite one another and disposed on the edge side.

4. The grid module of claim 1, wherein the at least partly broken-through sections are disposed, viewed in the longitudinal direction of the webs, equidistant from one another.

5. The grid module of claim 1, wherein exclusively one of the at least partly broken-through sections is disposed at at least one longitudinal position of the at least one grid web.

6. The grid module of claim 1, wherein a number of the at least partly broken-through sections are disposed along the web height at a longitudinal position of the at least one grid web.

7. The grid module of claim 3, wherein the at least partly broken-through sections on at least two opposing grid webs are disposed and are embodied in relation to their size such that all the at least partly broken-through sections of one grid web lie opposite a breakthrough-free surface of the respective other edge-side grid web.

8. The grid module of claim 1, wherein, in relation to a height of the at least one edge-side grid web, the number of the at least partly broken-through sections is equal to the number of breakthrough-free surfaces.

9. The grid module of claim 1, wherein at at least one of a minimum and maximum height of the at least one edge-side grid web, an end-to-end non-broken-through area is embodied over the entire length of the grid web.

10. The grid module of claim 1, wherein grid webs adjacent to the grid webs disposed at the edge side also have lateral at least partly broken-through sections.

11. The grid module of claim 10, wherein at least one of the number and overall surface of the at least partly broken-through sections in the grid webs reduces from the grid webs of the edge area of the grid module to the center of the grid module.

12. The grid module of claim 1, wherein grid webs running exclusively parallel in one direction are provided.

13. The grid module of claim 1, wherein grid webs crossing each other at right angles are provided.

14. The grid module of claim 1, wherein at least one edge-side grid web is provided from outside with a plastic film.

15. A scattered-radiation grid for an x-ray detector of a CT system including a plurality of detector elements disposed in rows and columns over its surface, comprising:
at least two grid modules arranged next to one another, each of the at least two grid modules possessing a number of grid webs disposed next to one another with irradiation zones between them, and at least one edge-side grid web of at least one of the grid modules being adjacent to at least one other web disposed running in parallel next to one another on the edge side of another of the grid modules in absence of an irradiation zone arranged between them, the grid webs adjoining each other and, without an intervening irradiation zone, each including a plurality of lateral breakthroughs, wherein the grid modules are embodied in accordance with claim 1.

16. A detector of a CT system with a modular-construction scattered-radiation grid, the scattered-radiation grid including the grid module of claim 1.

17. A CT system comprising a detector including a modular-construction scattered-radiation grid, the scattered-radiation grid including grid modules of claim 1.

18. The grid module of claim 2, wherein on at least one edge side of at least one of the grid modules, at least two grid webs are present with the at least partly broken-through sections opposite one another and disposed on the edge side.

19. The grid module of claim 2, wherein the at least partly broken-through sections are disposed, viewed in the longitudinal direction of the webs, equidistant from one another.

20. The grid module of claim 3, wherein the at least partly broken-through sections are disposed, viewed in the longitudinal direction of the webs, equidistant from one another.

21. The grid module of claim 20, wherein the at least partly broken-through sections and non-broken-through sections are arranged alternately.

22. The grid module of claim 20, wherein on at least one edge side of at least one of the grid modules, at least two grid webs are present with the at least partly broken-through sections opposite one another and disposed on the edge side.

23. The grid module of claim 20, wherein the at least partly broken-through sections are disposed, viewed in the longitudinal direction of the webs, equidistant from one another.

24. A scattered-radiation grid for an x-ray detector of a CT system including a plurality of detector elements disposed in rows and columns over its surface, comprising:
at least two grid modules arranged next to one another, each of the at least two grid modules possessing a number of grid webs disposed next to one another with irradiation zones between them, and at least one edge-side grid web of at least one of the grid modules being adjacent to at least one other web disposed running in parallel next to one another on the edge side of another of the grid modules in absence of an irradiation zone arranged between them, the grid webs adjoining each other and, without an intervening irradiation zone, each including a plurality of lateral breakthroughs.

25. The scattered-radiation grid of claim 24, wherein the lateral breakthroughs of adjacent edge-side grid webs are disposed such that the breakthroughs of a grid web are each covered by the adjoining edge-side other grid web.

26. The scattered-radiation grid of claim 24, wherein the breakthroughs are dimensioned in relation to their number and distribution so that the increased scattered-radiation reduction as a result of the presence of the double grid webs in the edge area of the grid module is compensated for by the breakthroughs.

27. The scattered-radiation grid of claim 25, wherein the breakthroughs are dimensioned in relation to their number and distribution so that the increased scattered-radiation reduction as a result of the presence of the double grid webs in the edge area of the grid module is compensated for by the breakthroughs.

28. A detector of a CT system comprising the scattered-radiation grid of claim 24.

29. A CT system comprising a detector including the scattered-radiation grid of claim 24.

* * * * *